(12) United States Patent
Safai

(10) Patent No.: US 8,879,688 B2
(45) Date of Patent: Nov. 4, 2014

(54) RECONFIGURABLE DETECTOR SYSTEM

(75) Inventor: Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 171 days.

(21) Appl. No.: 13/477,506

(22) Filed: May 22, 2012

(65) Prior Publication Data

US 2013/0315376 A1 Nov. 28, 2013

(51) Int. Cl.
*G01N 23/203* (2006.01)

(52) U.S. Cl.
USPC ............................................. 378/87; 378/86

(58) Field of Classification Search
USPC .................... 378/57, 86, 87, 88, 89
See application file for complete search history.

(56) References Cited

U.S. PATENT DOCUMENTS

| | | | |
|---|---|---|---|
| 6,243,441 B1 | 6/2001 | Zur | |
| 7,130,374 B1 | 10/2006 | Jacobs et al. | |
| 7,224,772 B2 | 5/2007 | Jacobs et al. | |
| 7,249,512 B2 | 7/2007 | Kennedy et al. | |
| 7,479,640 B2 | 1/2009 | Misawa | |
| 7,508,910 B2 | 3/2009 | Safai et al. | |
| 7,529,343 B2 | 5/2009 | Safai et al. | |
| 7,535,990 B2 | 5/2009 | Safai et al. | |
| 7,567,649 B1 | 7/2009 | Safai et al. | |
| 7,623,626 B2 | 11/2009 | Safai et al. | |
| 7,649,976 B2 | 1/2010 | Georgeson et al. | |
| 8,033,724 B2 | 10/2011 | Edwards et al. | |
| 2006/0162456 A1 | 7/2006 | Kennedy et al. | |
| 2006/0245547 A1* | 11/2006 | Callerame et al. | 378/87 |
| 2008/0310591 A1* | 12/2008 | Cason | 378/87 |
| 2011/0019799 A1* | 1/2011 | Shedlock | 378/87 |
| 2012/0002788 A1* | 1/2012 | Yang et al. | 378/88 |
| 2012/0033791 A1 | 2/2012 | Mastronardi | |

FOREIGN PATENT DOCUMENTS

WO WO2012142456 A2 10/2012

OTHER PUBLICATIONS

"Micro-PMT Technology," Hamamatsu Corporation, copyright 2010, Hamamatsu-Photonics West, 1 Page, accessed Apr. 20, 2012, http://sales.hamamatsu.com/info/pwest/micro-pmt.php.
Daniel et al., "Micro-electro-mechanical system fabrication technology applied to large area x-ray image sensor arrays," Journal of Vacuum Science & Technology, vol. 19, Issue 4, Jul. 2001, pp. 1219-1223.
Shedlock et al., "X-Ray Backscatter Imaging for Aerospace Applications," AIP Conference Proceedings, vol. 1335, Jul. 2010, pp. 509-516.
PCT search report dated May 8, 2013 regarding application PCT/US2013/027173, international filing date Feb. 21, 2013, applicant The Boeing Company, 11 pages.

* cited by examiner

*Primary Examiner* — Glen Kao
(74) *Attorney, Agent, or Firm* — Yee & Associates, P.C.

(57) ABSTRACT

A method and apparatus for inspecting an object using a backscatter inspection system. In one illustrative embodiment, an apparatus comprises a radiation source, a collimator, and a detector system. The radiation source is configured to emit radiation. The collimator is configured to form a beam using a portion of the radiation emitted by the radiation source. The beam is directed towards a surface of an object. The detector system is configured to detect backscatter formed in response to the beam encountering the object. A shape of the detector system is configured to be changed into a selected shape.

20 Claims, 6 Drawing Sheets

RECONFIGURABLE DETECTOR SYSTEM

BACKGROUND INFORMATION

1. Field

The present disclosure relates generally to inspection systems, and in particular, to backscatter inspection systems. Still more particularly, the present disclosure relates to a method and apparatus for detecting backscatter off of an object using a detector having a shape capable of substantially conforming to a shape of the object.

2. Background

A backscatter x-ray system is an example of a nondestructive inspection system (NDI) that uses x-rays to inspect an object. Some currently available backscatter x-ray systems include an x-ray tube, a collimator, and a detector. The x-ray tube generates and emits x-rays. The collimator filters these x-rays to form an x-ray beam using a portion of the x-rays that travel substantially parallel to a specified direction.

When the x-ray beam encounters the object, some or all of the x-rays in the x-ray beam are scattered by the object. In particular, the x-rays may be scattered off of the surface of the object and/or the subsurface of the object. The scattered x-rays are referred to as backscatter. The detector detects some or all of this backscatter. The detected backscatter may be used to generate image data for the object that can be used to form one or more images of the object. For example, the backscatter detected when the x-ray beam is directed at a particular location on the object may be used to generate an intensity value for a pixel in an image that corresponds to that particular location on the object.

The x-ray beam may be moved along the object in a selected pattern such as, for example, a raster pattern, such that image data may be generated for different locations on the object. In one illustrative example, the direction in which the x-ray beam is pointed may be changed such that the angle of incidence of the x-ray beam, with respect to the object, changes. This image data is used to form one or more images of the object that may be used to determine whether any inconsistencies are present in the object.

The detectors used in some currently available backscatter x-ray systems have a substantially planar shape. In other words, these detectors have a flat shape. The number of locations in which a backscatter x-ray system can be used may be limited when the detector in the backscatter x-ray system has a flat shape. For example, positioning a backscatter x-ray system with a detector having a flat shape relative to an object having a curved shape may be more difficult than desired.

Further, with a detector having a flat shape, the amount of backscatter detected by the detector may be less than desired for different angles of incidence of the x-ray beam with respect to the object when the object has a curved shape. In other words, the amount of backscatter detected by the detector may be less than desired for different angles of incidence of the x-ray beam when the object has a curved shape.

Consequently, images formed using the image data generated by a detector having a flat shape may not have a desired level of quality when used to detect backscatter off of a curved object. Therefore, it would be desirable to have a method and apparatus that takes into account at least some of the issues discussed above, as well as other possible issues.

SUMMARY

In one illustrative embodiment, an apparatus comprises a radiation source, a collimator, and a detector system. The radiation source is configured to emit radiation. The collimator is configured to form a beam using a portion of the radiation emitted by the radiation source. The beam is directed towards a surface of an object. The detector system is configured to detect backscatter formed in response to the beam encountering the object. A shape of the detector system is configured to be changed into a selected shape.

In another illustrative embodiment, a backscatter x-ray system comprises an x-ray tube, a collimator, and a detector system. The x-ray tube is configured to emit x-rays. The collimator is configured to form an x-ray beam using a portion of the x-rays emitted by the x-ray tube. The x-ray beam is directed towards a surface of an object. The detector system comprises a number of sensor arrays and a structure. The number of sensor arrays is configured to detect backscatter formed in response to the x-ray beam encountering the object. A shape of the detector system is configured to be changed into a selected shape using the structure.

In yet another illustrative embodiment, a method for inspecting an object is provided. A selected shape for a detector system in a backscatter inspection system is identified. A shape of the detector system is changed into the selected shape. A beam is emitted towards a surface of a object. The beam is formed using a portion of radiation emitted from a radiation source. Backscatter formed in response to the beam encountering the object is detected using the detector system having the selected shape.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account that images formed using the image data generated by some currently available backscatter x-ray systems may not have the desired amount of contrast. Without this desired amount of contrast, identifying inconsistencies in an object inspected using these backscatter x-ray systems may be more difficult than desired. In particular, the different illustrative embodiments recognize and take into account that a detector having a substantially planar shape may be unable to detect a desired amount of the backscatter formed when an x-ray beam encounters an object having a substantially nonplanar shape.

For example, the angle of incidence of an x-ray beam with respect to an object that has a curved shape may change when the x-ray beam is moved along the object. A detector having a flat shape may be unable to detect a desired amount of backscatter for these different angles of incidence of the x-ray beam with respect to the object. In other words, the detector may miss a portion of the backscatter when the object has a curved shape and the detector has a flat shape.

The different illustrative embodiments also recognize and take into account that the amount of backscatter detected by a detector determines the intensity value for a pixel in an image corresponding to the location at which the x-ray beam encounters the object. The intensity values for the pixels in an image may determine the level of contrast in the image and the level of detail in the image.

The image data generated by a detector having a flat shape may have a lower level of contrast and/or a lower level of detail than desired when the detector misses a portion of the backscatter formed as an x-ray beam moves along an object having a curved shape. Consequently, the different illustrative embodiments recognize and take into account that it may be desirable to have a detector configured to capture a greater portion of the backscatter formed as compared to currently available detectors.

Thus, the different illustrative embodiments provide a method and apparatus for inspecting an object using a backscatter x-ray system. In particular, the different illustrative embodiments provide a backscatter x-ray system with a detector having a shape that may be changed to substantially conform to a shape of a surface of the object being inspected.

Figure 1:
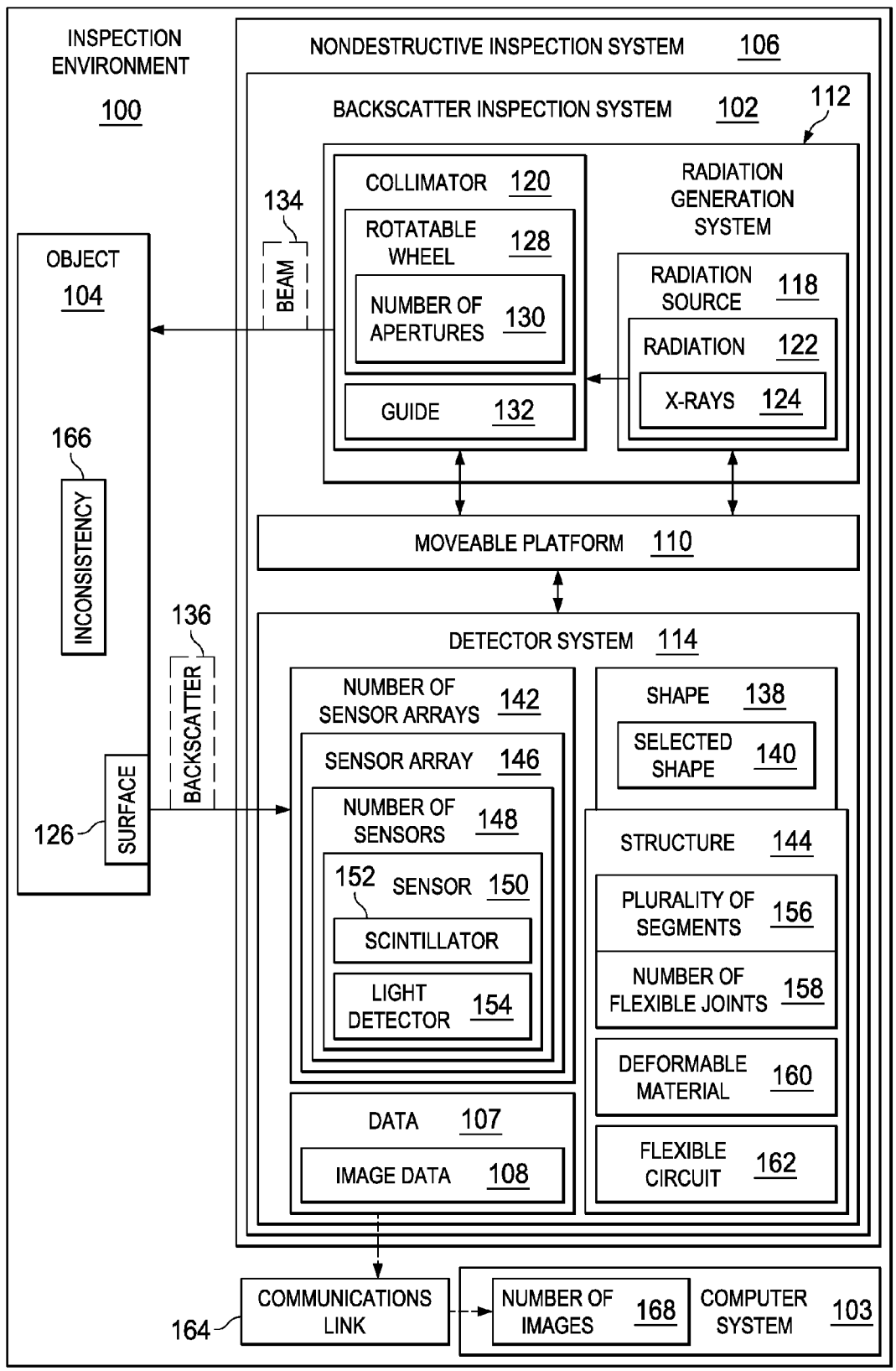
FIG. 1 is an illustration of an inspection environment in the form of a block diagram in accordance with an illustrative embodiment.

With reference now to the figures and, in particular, with reference to FIG. 1, an illustration of an inspection environment in the form of a block diagram is depicted in accordance with an illustrative embodiment. In these illustrative examples, inspection environment 100 includes backscatter inspection system 102, computer system 103, and object 104.

Backscatter inspection system 102 is one example of non-destructive inspection (NDI) system 106. As used herein, a "nondestructive inspection system", such as nondestructive inspection system 106, is a system configured to inspect an object, such as object 104, without causing any undesired effects to the object. In particular, a nondestructive inspection system is configured to inspect an object without causing any physical alterations to the object.

In these illustrative examples, backscatter inspection system 102 may be used to inspect object 104. Object 104 may be selected from any number of different types of objects. For example, without limitation, object 104 may take the form of a mobile platform, a stationary platform, an air-based structure, a land-based structure, an aquatic-based structure, a space-based structure, or some other suitable type of structure. More specifically, object 104 may be a an aircraft, a ship, a tank, a personnel carrier, a spacecraft, a space station, a satellite, a submarine, a vehicle, a manmade structure, a building, or some other suitable type of object.

In some cases, object 104 may be a part in another object. For example, in some cases, object 104 may be a section of a fuselage for an aircraft, a wing, a fuel tank, a structural support on a bridge, a section of a space station, the hull of a ship, a skin panel, a wall, a door, or some other suitable type of part.

Backscatter inspection system 102 generates data 107 for object 104 during inspection of object 104. Data 107 may include, for example, without limitation, image data 108 for object 104. Backscatter inspection system 102 sends data 107 to computer system 103. Computer system 103 is configured to receive and process data 107 generated by backscatter inspection system 102.

In this illustrative example, backscatter inspection system 102 includes moveable platform 110, radiation generation system 112, and detector system 114. Radiation generation system 112 and/or detector system 114 may be associated with moveable platform 110.

When one component is "associated" with another component, the association is a physical association in these depicted examples. For example, a first component, such as detector system 114, may be considered to be associated with a second component, such as moveable platform 110, by being secured to the second component, bonded to the second component, mounted to the second component, welded to the second component, fastened to the second component, and/or connected to the second component in some other suitable manner.

The first component also may be connected to the second component using a third component. Additionally, the first component may be considered to be associated with the second component by being formed as part of and/or an extension of the second component Moveable platform 110 may be any platform configured to move over a surface. This movement may include translation and/or rotation. Moveable platform 110 may take various forms depending on the particular implementation. In one illustrative example, moveable platform 110 may be a cart.

Moveable platform 110 may include movement devices such as, for example, without limitation, wheels, rollers, sliders, a track system, and other types of movement devices. These movement devices may allow moveable platform 110 to move or be moved on a surface, such as, for example, without limitation, a floor, a rail system, or some other suitable type of surface.

In one illustrative example, moveable platform 110 may be moved by a human operator pushing moveable platform 110. In another illustrative example, moveable platform 110 may be moved using a propulsion system in moveable platform 110.

In these illustrative examples, radiation generation system 112 comprises radiation source 118 and collimator 120. Radiation source 118 is configured to generate radiation 122. Radiation 122 comprises a plurality of rays. Radiation 122 may take a number of different forms. In these illustrative examples, radiation 122 may take the form of x-rays, gamma rays, or some other suitable type of radiation configured to at least partially penetrate object 104.

As one illustrative example, radiation source 118 may take the form of an x-ray tube configured to generate and emit x-rays 124. X-rays 124 may be directed towards surface 126 of object 104.

In these illustrative examples, collimator 120 may be associated with at least one of moveable platform 110 and radiation source 118. Collimator 120 is a device configured to filter the plurality of rays in radiation 122 such that only the portion of rays traveling parallel to a specified direction are allowed to pass through collimator 120.

In particular, collimator 120 uses a portion of radiation 122 to form beam 134. Beam 134 may be directed towards surface 126 of object 104. When radiation 122 takes the form of x-rays 124, beam 134 is referred to as an x-ray beam.

In one illustrative example, collimator 120 takes the form of rotatable wheel 128. Rotatable wheel 128 has number of apertures 130. As used herein, a "number of" items means one or more items. For example, number of apertures means one or more apertures. In this manner, number of apertures 130 may be one aperture in some cases and may be two, three, five, or some other suitable number of apertures in other cases.

Rotatable wheel 128 is configured to rotate around radiation source 118 while radiation source 118 emits radiation 122. As rotatable wheel 128 rotates, a portion of radiation 122 passes through an aperture in number of apertures 130 to form beam 134.

Of course, in other illustrative examples, collimator 120 may have guide 132. Guide 132 is a channel within collimator 120 through which rays may pass. In particular, collimator 120 may absorb a portion of the rays in radiation 122, scatter a portion of the rays in radiation 122, or perform a combination of the two such that only rays that travel in the direction of a center axis through guide 132 may pass through collimator 120.

Detector system 114 is configured to detect backscatter 136 formed in response to beam 134 encountering object 104. Backscatter 136 may be formed in response to at least a portion of beam 134 being scattered when beam 134 encounters surface 126 of object 104 and/or the subsurface of object 104. In these illustrative examples, detector system 114 has shape 138. Shape 138 of detector system 114 is configured to be changed into selected shape 140.

For example, selected shape 140 may be a surface shape for surface 126 of object 104 being inspected. The surface shape of surface 126 of object 104 may comprise, for example, without limitation, at least one of a convex shape, a concave shape, a wavy shape, a curved shape, an L-shape, a U-shape, a toroidal shape, or some other suitable type of substantially non-planar shape.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; or some other suitable combination.

In these illustrative examples, selected shape 140 for detector system 114 may be identified in a number of different ways. As one illustrative example, selected shape 140 may be identified from a database of known geometries for different types of objects to be inspected. For example, selected shape 140 may be identified using a digital computer aided design (CAD) model of the object 104 stored in a database.

In some illustrative examples, selected shape 140 may be identified using images of object 104 to be inspected. Selected shape 140 may also be identified using sensor data generated while detector system 114 is positioned relative to object 104 being inspected. For example, a number of sensor systems may be used to generate images, ultrasound images, acoustic data, radar images, infrared images, and/or other suitable types of sensor data that can be used to identify selected shape 140. Of course, selected shape 140 may be identified in other ways not described above.

In one illustrative example, detector system 114 comprises number of sensor arrays 142 and structure 144. Number of sensor arrays 142 is associated with structure 144 in this illustrative example. Sensor array 146 is an example of one of number of sensor arrays 142. Sensor array 146 comprises number of sensors 148 arranged in a number of rows and in a number of columns. Sensor 150 is an example of one of number of sensors 148.

In some illustrative examples, sensor 150 may also be referred to as a detector. In this manner, number of sensors 148 may be a number of detectors, sensor array 146 may be a detector array, and number of sensor arrays 142 may be a number of detector arrays.

In this illustrative example, sensor 150 may comprise scintillator 152 and light detector 154. Scintillator 152 may comprise a material configured to luminesce when hit by ionizing radiation, such as, for example, the particles of backscatter 136. This material is referred to as a scintillating material. When scintillator 152 luminesces, photons are emitted from the scintillator 152.

Light detector 154 is configured to measure the number of photons emitted from scintillator 152. The number of photons detected by all of the light detectors in number of sensor arrays 142 may determine the value generated by detector system 114 for the particular location on object 104 at which beam 134 was pointed. This value may be an intensity value for a pixel in an image of object 104 corresponding to the location at which beam 134 was pointed. Shape 138 of detector system 114 may be changed such that the number of photons detected by the different light detectors in number of sensor arrays 142 as beam 134 moves along surface 126 of object 104 allows image data having a desired level of detail and a desired level of contrast to be generated.

In this illustrative example, light detector 154 may have a configuration based on micro-electromechanical systems (MEMS) technology. For example, light detector 154 may be selected from one of a photomultiplier tube (PMT), a photoelectric sensor, a photodiode, or some other type of light detector implemented using micro-electromechanical systems technology. In one illustrative example, light detector 154 takes the form of a micro-photomultiplier tube (micro-PMT o μ-PMT).

When sensor 150 includes scintillator 152 and light detector 154, sensor 150 may take the form of a scintillation detector or a scintillation counter. Of course, in other illustrative examples, sensor 150 may take the form of a solid-state detector, a semiconductor radiation detector, or some other suitable type of detector.

In this illustrative example, shape 138 of detector system 114 may be changed using structure 144. For example, structure 144 may comprise plurality of segments 156 connected to each other through number of flexible joints 158. Movement of at least one segment in plurality of segments 156 relative to another segment in plurality of segments 156 about a flexible joint in number of flexible joints 158 changes shape 138 of detector system 114. When structure 144 has this type of configuration, structure 144 may be referred to as an "articulated structure."

A segment in plurality of segments 156 may be moved relative to another segment in plurality of segments 156 in a number of different ways. For example, these segments may be moved manually. A human operator may use his hands to move one or more of plurality of segments 156 about one or more of number of flexible joints 158. In some cases, plurality of segments 156 may be moved by an electromechanical system configured to receive commands from a control system.

In another example, structure 144 may take the form of deformable material 160. Deformation of deformable material 160 changes shape 138 of detector system 114. Deformable material 160 may comprise, for example, without limitation, an organic material, a silicon-based material, or some other suitable type of material capable of being deformed. Deformable material 160 may be deformed manually in these illustrative examples.

In some illustrative examples, structure 144 may take the form of flexible circuit 162. Flexible circuit 162 may comprise any number of lines and controls having a configuration that may be changed when power is supplied to these lines and controls. Changing a configuration of flexible circuit 162 changes shape 138 of detector system 114.

In this manner, shape 138 of detector system 114 may be changed in a number of different ways. Shape 138 of detector system 114 may be reconfigurable using structure 144. In particular, shape 138 may be changed into selected shape 140 such that shape 138 of detector system 114 substantially conforms to a surface shape for surface 126 of object 104.

In some illustrative examples, an electromechanical system may be used to reconfigure structure 144 based on input received from a digital model of object 104. In other illustrative examples, structure 144 may be reconfigured manually to substantially match selected shape 140. Further, depending on the implementation, structure 144 may be repeatedly reconfigured as moveable platform 110 moves relative to object 104. Sensor data, such as images or video of object 104, may be used to change shape 138 of detector system 114 such that shape 138 substantially conforms to a surface shape for surface 126 of object 104 as moveable platform 110 with detector system 114 moves relative to object 104.

Detector system 114 generates data 107 in response to detecting backscatter 136. Image data 108 in data 107 may include, for example, an intensity value for a pixel corresponding to each of a plurality of locations on object 104 at which beam 134 was directed.

Detector system 114 sends data 107 to computer system 103 for processing using communications link 164. Communications link 164 may be a wireless communications link, a wired communications link, an optical communications link, or some other suitable type of communications link.

Computer system 103 may include one or more computers, depending on the implementation. When more than one computer is present in computer system 103, these computers may be in communication with each other using a medium such as a network. The network may employ wired communications links, wireless communications links, and other suitable types of links for exchanging information.

Data 107 may be used to determine whether inconsistency 166 is present in object 104. Inconsistency 166 may be present at surface 126 of object 104 or within an interior of object 104. In one illustrative example, computer system 103 uses data 107 to form number of images 168 of object 104. Number of images 168 may be analyzed by computer system 103 and/or a human operator to detect the presence of, and identify the location of, inconsistency 166 in object 104. Of course, in other illustrative examples, image data 108 in data 107 generated by detector system 114 may take the form of number of images 168.

Depending on the implementation, computer system 103 may be configured to control at least one of radiation generation system 112, moveable platform 110, and detector system 114. For example, computer system 103 may send commands to moveable platform 110 and/or collimator 120 to control the steering of beam 134. In some cases, computer system 103 may send commands to detector system 114 to control shape 138 of detector system 114. For example, computer system 103 may send commands to flexible circuit 162 to change shape 138 of detector system 114.

With the different configurations for detector system 114 described in FIG. 1, less radiation 122 may need to be emitted from radiation source 118. Further, the size of radiation source 118 as well as the overall size of backscatter inspection system 102 may be reduced with detector system 114 having shape 138 that is reconfigurable. Additionally, using microelectromechanical systems technology may allow number of sensor arrays 142 to be manufactured in a cost-effective and efficient manner.

The illustration of inspection environment 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

In some illustrative examples, the different sensors in number of sensor arrays 142 may not include scintillators. Instead, a single piece of scintillating material may be placed over each sensor array in number of sensor arrays 142. In some cases, a single piece of scintillating material may be placed over all of the sensor arrays in number of sensor arrays 142.

Figure 2:
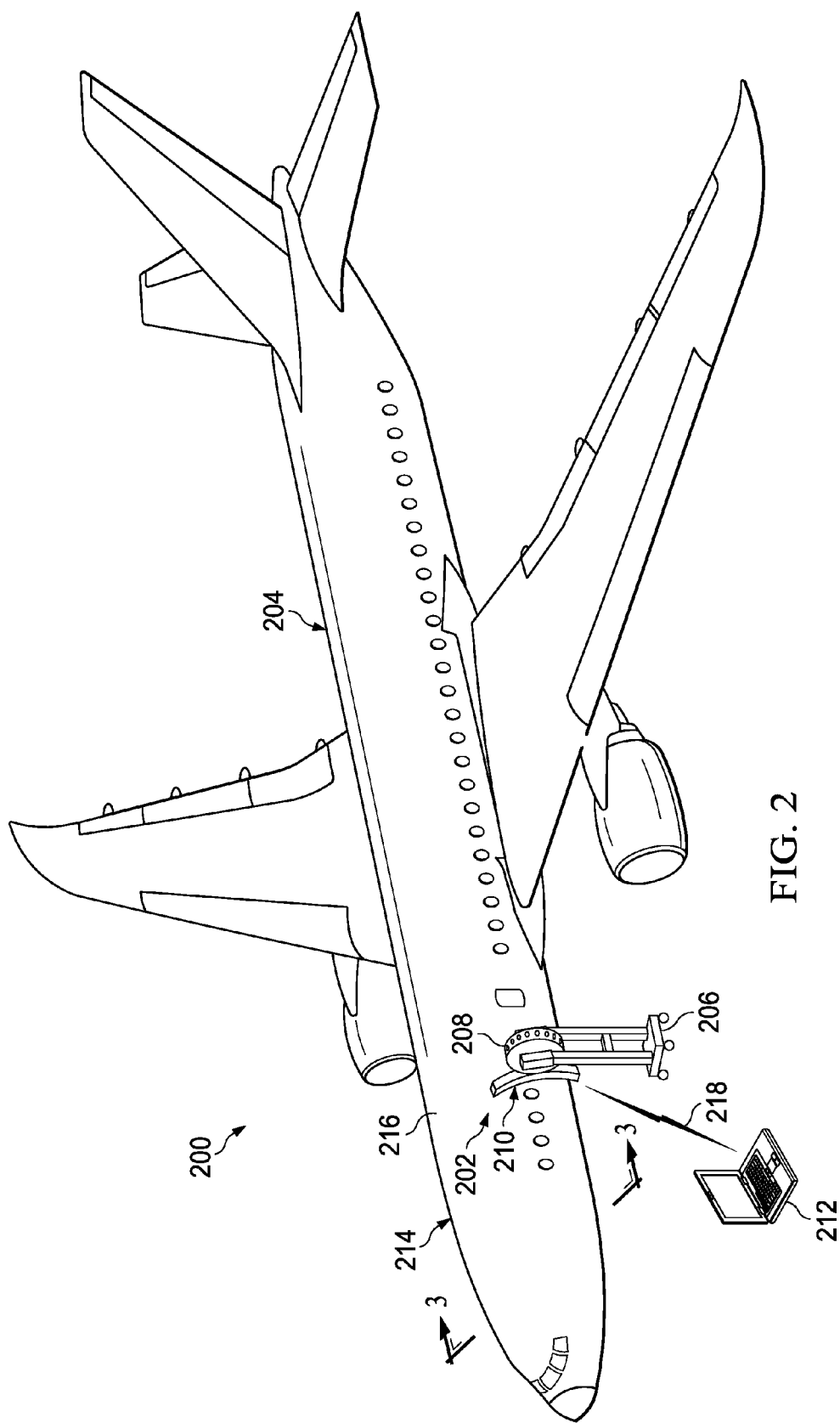
FIG. 2 is an illustration of an inspection environment in accordance with an illustrative embodiment.

With reference now to FIG. 2, an illustration of an inspection environment is depicted in accordance with an illustrative embodiment. In FIG. 2, inspection environment 200 is an example of one implementation for inspection environment 100 in FIG. 1. Backscatter inspection system 202 is configured to perform an inspection of aircraft 204 in inspection environment 200.

Backscatter inspection system 202 is an example of one implementation for backscatter inspection system 102 in FIG. 1. In this illustrative example, backscatter inspection system 202 is a backscatter x-ray system. Further, aircraft 204 is an example of one implementation for object 104 in FIG. 1.

As depicted, backscatter inspection system 202 includes moveable platform 206, radiation generation system 208, detector system 210, and computer system 212. Moveable platform 206, radiation generation system 208, detector system 210, and computer system 212 are examples of implementations for moveable platform 110, radiation generation system 112, detector system 114, and computer system 103, respectively, in FIG. 1.

In this illustrative example, radiation generation system 208 and detector system 210 are connected to moveable platform 206. Computer system 212 is located away from moveable platform 206.

Radiation generation system 208 is configured to generate x-rays and direct a portion of these x-rays towards fuselage 214 of aircraft 204 in the form of an x-ray beam. In particular, radiation generation system 208 directs the x-ray beam towards surface 216 of fuselage 214 of aircraft 204. Surface 216 is an exterior surface of fuselage 214. Additionally, radiation generation system 208 may move the x-ray beam along surface 216 of fuselage 214 such that the angle of incidence of the x-ray beam with respect to surface 216 of fuselage 214 changes.

The x-ray beam may at least partially penetrate surface 216 of fuselage 214 of aircraft 204. Detector system 210 is configured to detect backscatter formed in response to the x-ray beam encountering fuselage 214. Detector system 210 may generate image data that is sent to computer system 212 over wireless communications link 218. Detector system 210 is described in greater detail in FIGS. 3-4.

Figure 3:
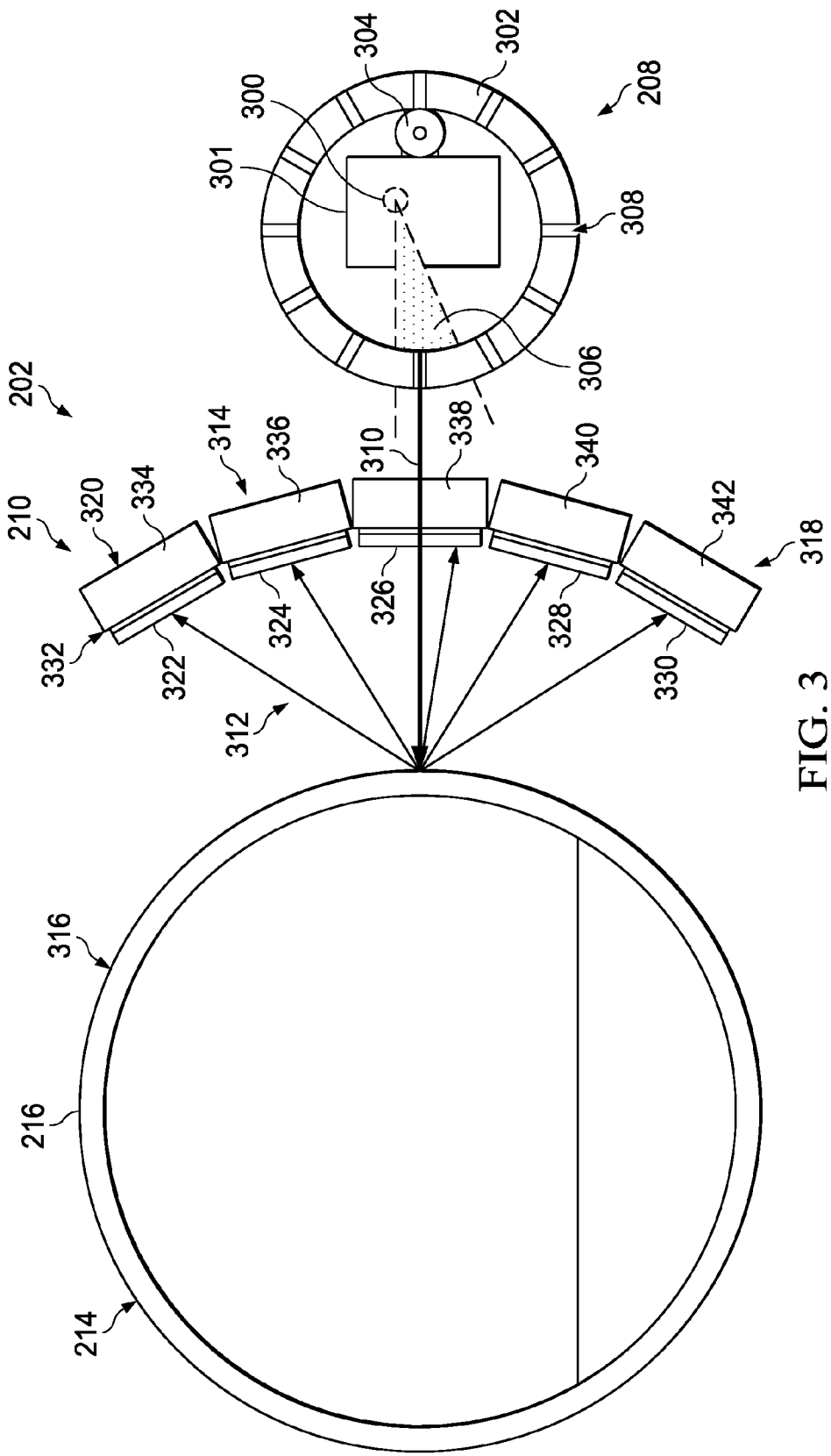
FIG. 3 is an illustration of a cross-sectional view of an aircraft being inspected by a backscatter inspection system in accordance with an illustrative embodiment.

Turning now to FIG. 3, an illustration of a cross-sectional view of an aircraft being inspected by a backscatter inspection system is depicted in accordance with an illustrative embodiment. In this illustrative example, a cross-sectional view of aircraft 204 from FIG. 2, taken along lines 3-3, is depicted along with backscatter inspection system 202. Moveable platform 206 of backscatter inspection system 202 is not shown in this view such that radiation generation system 208 may be more clearly seen.

In this illustrative example, radiation generation system 208 includes radiation source 300, housing 301, rotatable wheel 302, and motor 304. Radiation source 300 is an example of one implementation for radiation source 118 in FIG. 1. As depicted, radiation source 300 is located within housing 301. Housing 301 may be connected to moveable platform 206 in FIG. 2. Radiation source 300 is configured to generate and emit x-rays 306.

Rotatable wheel 302 is associated with radiation source 300. Rotatable wheel 302 is an example of one implementation for rotatable wheel 128 in FIG. 1. Rotatable wheel 302 has number of apertures 308. Operation of motor 304 is configured to rotate rotatable wheel 302 such that number of apertures 308 rotate around radiation source 300.

As rotatable wheel 302 rotates, a portion of x-rays 306 is configured to pass through an aperture in number of apertures 308 to form x-ray beam 310. X-ray beam 310 is directed towards surface 216 of fuselage 214. The x-rays in x-ray beam 310 scatter in response to encountering fuselage 214. These scattered x-rays form backscatter 312.

Detector system 210 detects backscatter 312. As depicted, detector system 210 has shape 314. Shape 314 is reconfigurable. In other words, shape 314 of detector system 210 may be changed.

In this illustrative example, shape 314 is configured to substantially conform to surface shape 316 of surface 216 of fuselage 214. In particular, shape 314 is a convex shape with respect to radiation generation system 208 that is similar to surface shape 316 of surface 216 of fuselage 214, which is also a convex shape with respect to radiation generation system 208.

In this illustrative example, detector system 210 includes number of sensor arrays 318 and structure 320. As depicted, number of sensor arrays 318 includes sensor arrays 322, 324, 326, 328, and 330. These sensor arrays are associated with structure 320. The shape of structure 320 is shape 314 of detector system 210. In this manner, both detector system 210 and structure 320 have shape 314.

Structure 320 comprises plurality of segments 332. Plurality of segments 332 includes segments 334, 336, 338, 340, and 342. Sensor arrays 322, 324, 326, 328, and 330 are associated with segments 334, 336, 338, 340, and 342, respectively. Segments 334, 336, 338, 340, and 342 may be connected to each other by flexible joints. For example, segment 334 may be configured to move relative to segment 336 about a flexible joint connecting segment 334 and segment 336. When segment 334 moves relative to segment 336, sensor array 322 also moves relative to sensor array 324.

One or more segments in plurality of segments 332 may be moved relative to each other such that structure 320 may have shape 314 that substantially conforms to surface shape 316 of surface 216 of fuselage 214. For example, structure 320 may be bent at one or more of the flexible joints connecting plurality of segments 332 such that shape 314 of structure 320 changes to substantially conform to surface shape 316 of surface 216 of fuselage 214.

Figure 4:
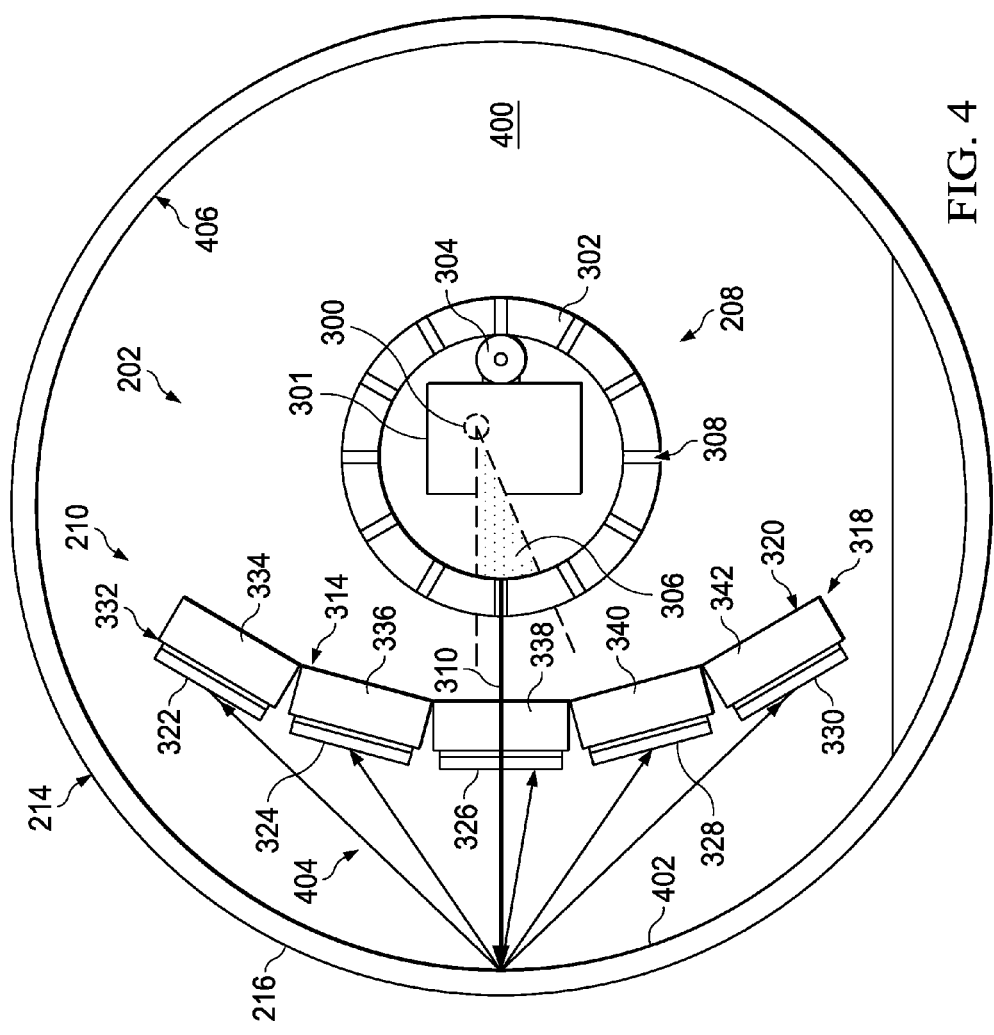
FIG. 4 is an illustration of a cross-sectional view of an aircraft being inspected by a backscatter inspection system in accordance with an illustrative embodiment.

Turning now to FIG. 4, an illustration of a cross-sectional view of an aircraft being inspected by a backscatter inspection system is depicted in accordance with an illustrative embodiment. In this illustrative example, the cross-sectional view of aircraft 204 from FIG. 3 is depicted with backscatter inspection system 202 moved into interior 400 of fuselage 214.

In this illustrative example, radiation generation system 208 is configured to direct x-ray beam 310 towards surface 402 of fuselage 214. Surface 402 is an interior surface of fuselage 214. Backscatter 404 is formed in response to x-ray beam 310 encountering fuselage 214.

As depicted, shape 314 of detector system 210 has been changed such that shape 314 substantially conforms to surface shape 406 of surface 402 of fuselage 214. In particular, surface shape 406 of surface 402 has a concave shape with respect to radiation generation system 208. Structure 320 of detector system 210 has been bent at one or more flexible joints between plurality of segments 332 such that shape 314 of structure 320 has a concave shape with respect to radiation generation system 208 that is similar to the concave shape of surface 402 of fuselage 214.

In this manner, when shape 314 of detector system 210 substantially conforms to surface shape 406 of surface 402 of fuselage 214, detector system 210 and radiation generation system 208 in backscatter inspection system 202 may be moved closer to surface 402. The amount of backscatter 404 detected by detector system 210 increases as detector system 210 moves closer to surface 402.

Figure 5:
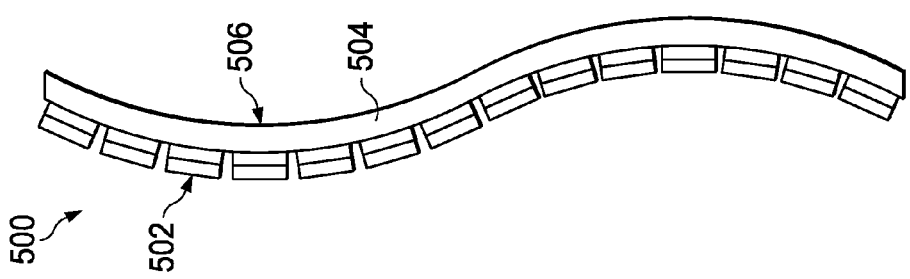
FIG. 5 is an illustration of a detector system in accordance with an illustrative embodiment.

With reference now to FIG. 5, an illustration of a detector system is depicted in accordance with an illustrative embodiment. In this illustrative example, detector system 500 is an example of one implementation for detector system 114 in FIG. 1. As depicted, detector system 500 includes number of sensor arrays 502 associated with structure 504. Structure 504 takes the form of a deformable material in this example. Structure 504 is configured to be deformed such that structure 504 may have a desired shape. In this depicted example, structure 504 has wavy shape 506.

Figure 6:
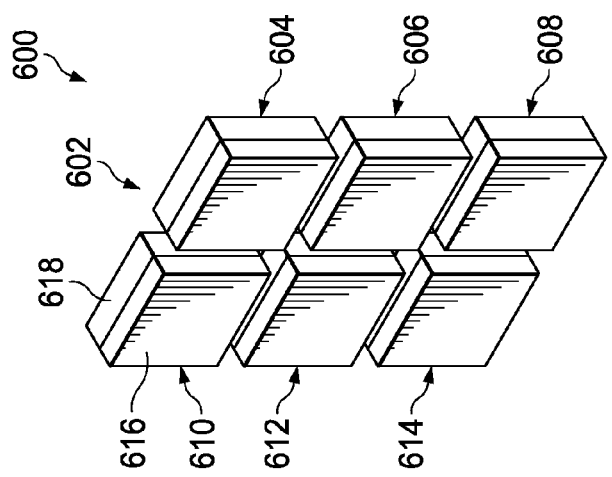
FIG. 6 is an illustration of a sensor array in accordance with an illustrative embodiment.

Turning now to FIG. 6, an illustration of a sensor array is depicted in accordance with an illustrative embodiment. In this illustrative example, sensor array 600 is an example of one sensor array in number of sensor arrays 502 in FIG. 5. As depicted, sensor array 600 comprises number of sensors 602 arranged in two columns and three rows. Number of sensors 602 includes sensors 604, 606, 608, 610, 612, and 614.

Each sensor in number of sensors 602 includes a scintillator and a light detector. For example, sensor 604 includes scintillator 616 and light detector 618. In this illustrative example, light detector 618 is a micro-photomultiplier tube. Of course, in other illustrative examples, light detector 618 may be some other suitable type of light detector.

Figure 7:
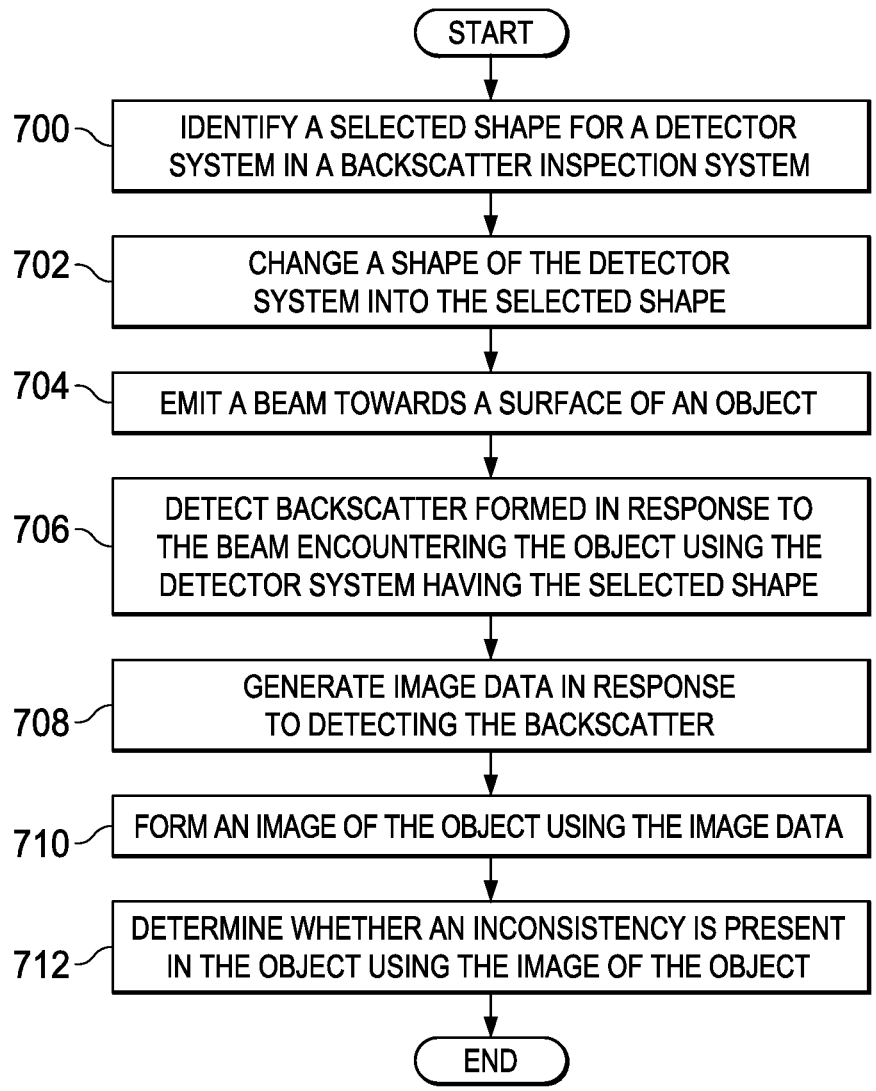
FIG. 7 is an illustration of a process for inspecting an object, in the form of a flowchart, in accordance with an illustrative embodiment.

With reference now to FIG. 7, an illustration of process for inspecting an object, in the form of a flowchart, is depicted in accordance with an illustrative embodiment. The process illustrated in FIG. 7 may be used to inspect an object, such as object 104 in FIG. 1. This process may be implemented using, for example, without limitation, backscatter inspection system 102 in FIG. 1.

The process begins by identifying a selected shape for a detector system in a backscatter inspection system (operation 700). In operation 700, the detector system may be detector system 114 in FIG. 1. The process then changes a shape of the detector system into the selected shape (operation 702). In operation 702, the shape of the detector system may be changed in a number of different ways using a structure in the detector system. The structure may be, for example, structure 144 in FIG. 1.

When the structure is a plurality of segments connected to each other by a number of flexible joints, operation 702 may be performed by moving at least one of the segments in the plurality of segments relative to another segment in the plurality of segments about a flexible joint in the number of flexible joints. When the structure is a deformable material, operation 702 may be performed by deforming the deformable material.

Further, when the structure is a flexible circuit, operation 702 may be performed by sending commands to the flexible circuit to cause a configuration of the flexible circuit to change. Changing the configuration of the flexible circuit may change the shape of the detector system.

Thereafter, the process emits a beam towards a surface of an object (operation 704). The beam is formed using a portion of radiation emitted from a radiation source in the backscatter inspection system. Next, the process detects backscatter formed in response to the beam encountering the object using the detector system having the selected shape (operation 706). The backscatter may be formed in response to at least a portion of the beam being scattered when the beam encounters the surface of the object and/or the subsurface of the object.

The process generates image data in response to detecting the backscatter (operation 708). The process then forms an image of the object using the image data (operation 710). The process then determines whether an inconsistency is present in the object using the image of the object (operation 712), with the process terminating thereafter.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Thus, the different illustrative embodiments provide a method and apparatus for inspecting an object. In one illustrative embodiment, an apparatus comprises a radiation source, a collimator, and a detector system. The radiation source is configured to emit radiation. The collimator is configured to form a beam using a portion of the radiation emitted by the radiation source. The beam is directed towards a surface of an object. The detector system is configured to detect backscatter formed in response to the beam encountering the object. A shape of the detector system is configured to be changed into a selected shape.

The different illustrative embodiments provide a detector system that allows a smaller radiation source to be used in a backscatter inspection system. Further, with a detector system that has a shape that is reconfigurable, the size of the overall backscatter inspection system may be reduced. Still further, using light detectors based on micro-electromechanical systems technology in a detector system may reduce the cost of the detector system as compared to currently available detector systems.

The description of the different illustrative embodiments has been presented for purposes of illustration and description, and is not intended to be exhaustive or limited to the embodiments in the form disclosed. Many modifications and variations will be apparent to those of ordinary skill in the art.

Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a radiation source configured to emit radiation, wherein the radiation comprises x-rays configured to at least partially penetrate an object;
a collimator configured to form a beam using a portion of the radiation emitted by the radiation source, wherein the beam is directed towards a surface of the object;
a detector system configured to detect backscatter formed in response to the beam encountering the object in which a shape of the detector system is configured to be changed from a first shape of the detector system to a second shape of the detector system using a structure in the detector system, wherein the second shape of the detector system substantially conforms to a substantially non-planar shape of the surface of the object, wherein the first shape of the detector system and the second shape of the detector system are different, and wherein the second shape of the detector system is a selected shape of the detector system, wherein the detector system comprises a number of sensors associated with the structure and configured to detect the backscatter; and
an electromechanical system configured to repeatedly reconfigure the structure as a moveable platform moves relative to the object; and
wherein:
the moveable platform is associated with the detector system;
the electromechanical system repeatedly reconfigures the structure using data from the number of sensors; and
the electromechanical system repeatedly reconfigures the structure such that the shape of the detector system changes to substantially conform to the substantially non-planar shape of the surface of the object.

2. The apparatus of claim 1, wherein the detector system comprises:
the structure, wherein the shape of the detector system is configured to be changed into the selected shape using the structure; and
a number of sensor arrays comprising the number of sensors and associated with the structure, wherein the number of sensor arrays is configured to detect the backscatter formed in response to the beam encountering the object.

3. The apparatus of claim 2, wherein the structure comprises:
a plurality of segments connected to each other by a number of flexible joints, wherein movement of at least one segment in the plurality of segments relative to another segment in the plurality of segments about a flexible joint in the number of flexible joints changes the shape of the detector system.

4. The apparatus of claim 2, wherein the structure comprises:
a deformable material, wherein deformation of the deformable material changes the shape of the detector system.

5. The apparatus of claim 2, wherein the structure comprises:
a flexible circuit, wherein changing a configuration of the flexible circuit changes the shape of the detector system.

6. The apparatus of claim 2, wherein a sensor array in the number of sensor arrays comprises:
the number of sensors arranged in a number of rows and a number of columns.

7. The apparatus of claim 6, wherein a sensor in the number of sensors comprises a scintillator and a light detector and the sensor is selected from one of a scintillation detector and a scintillation counter.

8. The apparatus of claim 2, wherein the radiation source and the collimator form a radiation generation system and further comprising:
the moveable platform, wherein at least one of the radiation generation system and the detector system are associated with the moveable platform; and
a housing connected to the moveable platform, wherein the radiation source is located inside the housing.

9. The apparatus of claim 8,
wherein:
the data from the number of sensors comprises at least one of images of the object and video of the object.

10. The apparatus of claim 2, wherein the radiation source is an x-ray tube, and the beam is an x-ray beam and wherein each of the number of sensor arrays is substantially equidistant from the substantially non-planar shape of the surface of the object relative to all other sensor arrays in the number of sensor arrays.

11. The apparatus of claim 1, wherein the selected shape substantially conforms to the substantially non-planar shape of the surface of the object and wherein the substantially non-planar shape of the surface of the object and the selected shape comprise at least one of a wavy shape, a curved shape, and a toroidal shape.

12. The apparatus of claim 1, wherein the collimator comprises:
a rotatable wheel having a number of apertures, wherein the rotatable wheel is configured to rotate while the radiation source emits the radiation in which the portion of the radiation emitted by the radiation source passes through an aperture in the number of apertures to form the beam.

13. A backscatter x-ray system comprising:
an x-ray tube configured to emit x-rays;
a collimator configured to form an x-ray beam using a portion of the x-rays emitted by the x-ray tube, wherein the x-ray beam is directed towards a surface of an object;
a detector system comprising:
a number of sensor arrays comprising a number of sensors and configured to detect backscatter formed in response to the x-ray beam encountering the object; and
a structure, wherein a shape of the detector system is configured to be changed from a first shape of the detector system to a second shape of the detector system using the structure, wherein the second shape of the detector system substantially conforms to a substantially non-planar surface shape of the object, wherein the second shape of the detector system is different from the first shape of the detector system, and wherein the second shape of the detector system is a selected shape of the detector system; and
an electromechanical system configured to repeatedly reconfigure the structure as a moveable platform moves relative to the object; and
wherein:
the moveable platform is associated with the detector system;
the electromechanical system repeatedly reconfigures the structure using data from the number of sensors; and
the electromechanical system repeatedly reconfigures the structure such that the shape of the detector system changes to substantially conform to the substantially non-planar shape of the surface of the object.

14. The backscatter x-ray system of claim 13, wherein the structure is an articulated structure comprising:
a plurality of segments connected to each other by a number of flexible joints, wherein movement of at least one segment in the plurality of segments relative to another segment in the plurality of segments about a flexible joint in the number of flexible joints changes the shape of the detector system from the first shape of the detector system to the second shape of the detector system.

15. The backscatter x-ray system of claim 13, wherein each of the number of sensor arrays is substantially equidistant from the substantially non-planar shape of the surface of the object relative to all other sensor arrays in the number of sensor arrays.

16. The backscatter x-ray system of claim 13, wherein the selected shape substantially conforms to the substantially non-planar surface shape of the object and wherein the substantially non-planar surface shape of the object and the selected shape comprise at least one of a wavy shape, a curved shape, and a toroidal shape.

17. A method for inspecting an object, the method comprising:
identifying a selected shape for a detector system in a backscatter inspection system, wherein the selected shape comprises a substantially non-planar surface shape of the object;
changing a shape of the detector system from a first shape of the detector system to a second shape of the detector system using a structure in the detector system, wherein the second shape of the detector system substantially conforms to the substantially non-planar surface shape of the object, wherein the first shape of the detector system and the second shape of the detector system are different, wherein the second shape of the detector system is the selected shape for the detector system, and wherein a number of sensor arrays in the detector system configured to detect the backscatter are associated with the structure;
emitting a beam towards a surface of the object, wherein the beam is formed using a portion of radiation emitted from a radiation source, wherein the radiation comprises x-rays configured to at least partially penetrate the object; detecting backscatter formed in response to the beam encountering the object using the detector system having the selected shape; and
repeatedly reconfiguring the structure as a moveable platform moves relative to the object using an electromechanical system; and
wherein:
the moveable platform is associated with the detector system;

the step of repeatedly reconfiguring the structure uses data from the number of sensors; and the step of repeatedly reconfiguring the structure changes the shape of the detector system to substantially conform to the substantially non-planar surface of the object.

18. The method claim 17, wherein:

the data from the number of sensors comprises at least one of images of the object and video of the object.

19. The method of claim 18, wherein the radiation comprises x-rays and wherein each of the number of sensor arrays is substantially equidistant from the substantially non-planar shape of the surface of the object relative to all other sensor arrays in the number of sensor arrays.

20. The method of claim 17 further comprising:

generating image data in response to detecting the backscatter;

forming an image of the object using the image data; and determining whether an inconsistency is present in the object using the image of the object, wherein the selected shape substantially conforms to the substantially non-planar surface shape of the object, and wherein the substantially non-planar surface shape of the object and the selected shape comprise at least one of a wavy shape, a curved shape, and a toroidal shape.

* * * * *